(12) United States Patent
Klentzman

(10) Patent No.: US 9,651,459 B2
(45) Date of Patent: May 16, 2017

(54) GASOLINE BLEND SPOT SAMPLING SYSTEM AND METHOD

(71) Applicant: Welker, Inc., Sugar Land, TX (US)

(72) Inventor: James T. Klentzman, Richmond, TX (US)

(73) Assignee: Welker, Inc., Sugar Land, TX (US)

( * ) Notice: Subject to any disclaimer, the term of this patent is extended or adjusted under 35 U.S.C. 154(b) by 0 days.

(21) Appl. No.: 14/995,315

(22) Filed: Jan. 14, 2016

(65) Prior Publication Data

US 2016/0131558 A1 May 12, 2016

Related U.S. Application Data

(62) Division of application No. 13/754,996, filed on Jan. 31, 2013, now Pat. No. 9,255,862.

(51) Int. Cl.
*G01N 1/14* (2006.01)
*G01N 1/10* (2006.01)
*G01N 1/20* (2006.01)

(52) U.S. Cl.
CPC ............... *G01N 1/14* (2013.01); *G01N 1/10* (2013.01); *G01N 1/2035* (2013.01); *G01N 2001/1454* (2013.01); *G01N 2001/2057* (2013.01); *G01N 2001/2085* (2013.01)

(58) Field of Classification Search
CPC .......... G01N 1/10; G01N 1/14; G01N 1/2035; G01N 2001/1454; G01N 2001/2057; G01N 2001/2085
USPC ......................................... 73/863.11, 864.35
See application file for complete search history.

(56) References Cited

U.S. PATENT DOCUMENTS

| | | |
|---|---|---|
| 3,469,453 A | 9/1969 | Nelson |
| 4,077,263 A | 3/1978 | Brailsford |
| 4,101,282 A | 7/1978 | Ririe |
| 4,355,539 A | 10/1982 | Schatz |
| 4,418,581 A | 12/1983 | Jones |
| 4,440,032 A | 4/1984 | Welker |
| 4,475,410 A | 10/1984 | Jaeger |
| 4,532,813 A | 8/1985 | Rinehart |
| 4,651,574 A | 3/1987 | Spencer |
| 4,706,495 A * | 11/1987 | Steudle ............... G01N 13/04 73/64.47 |
| 4,712,434 A * | 12/1987 | Herwig ............... G01N 1/2035 73/863.71 |
| 4,887,472 A | 12/1989 | Jansen |
| 5,301,560 A | 4/1994 | Anderson et al. |

(Continued)

OTHER PUBLICATIONS

MD-Flow Thru, Texas Sampling Systems of Victoria, TX; www.texassampling.com, retrieved as early as Jan. 16, 2013.

(Continued)

*Primary Examiner* — Daniel S Larkin
(74) *Attorney, Agent, or Firm* — Husch Blackwell LLP

(57) ABSTRACT

A gasoline blend spot sampling system and method including an adjustable volume mechanism for retaining an adjustable volume of gasoline for sampling, a coolant system integrated with the adjustable volume mechanism, and a sample collection assembly using a blunt-end tube for use with an open-mouthed bottle. Various three-way valves are actuated to route gasoline through various stages of a sampling process, from a gasoline fast loop to a purge loop to a gasoline capture stage to a sample bottling stage.

1 Claim, 14 Drawing Sheets

(56) References Cited

U.S. PATENT DOCUMENTS

| | | |
|---|---|---|
| 5,361,643 A | 11/1994 | Boyd |
| 5,394,736 A | 3/1995 | Barnett |
| 5,431,067 A | 7/1995 | Anderson et al. |
| 5,433,120 A | 7/1995 | Boyd et al. |
| 5,665,314 A | 9/1997 | Berger et al. |
| 5,945,611 A | 8/1999 | Welker |
| 6,682,939 B2 | 1/2004 | Diaz |
| 8,210,058 B2 | 7/2012 | Welker et al. |
| 2011/0192237 A1 | 8/2011 | Bombulie et al. |

OTHER PUBLICATIONS

DOPAK Process Sampler Type S23 configuration with cooling/heating jacket (D3), Dopak, Inc., www.dopak.com, retrieved as early as Jan. 16, 2013.

\* cited by examiner

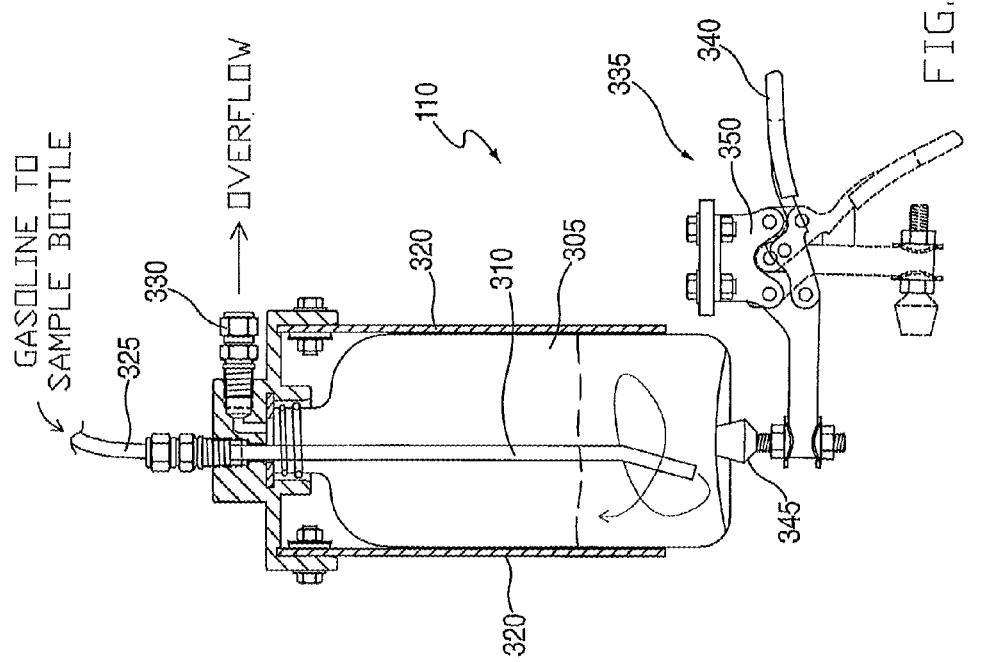
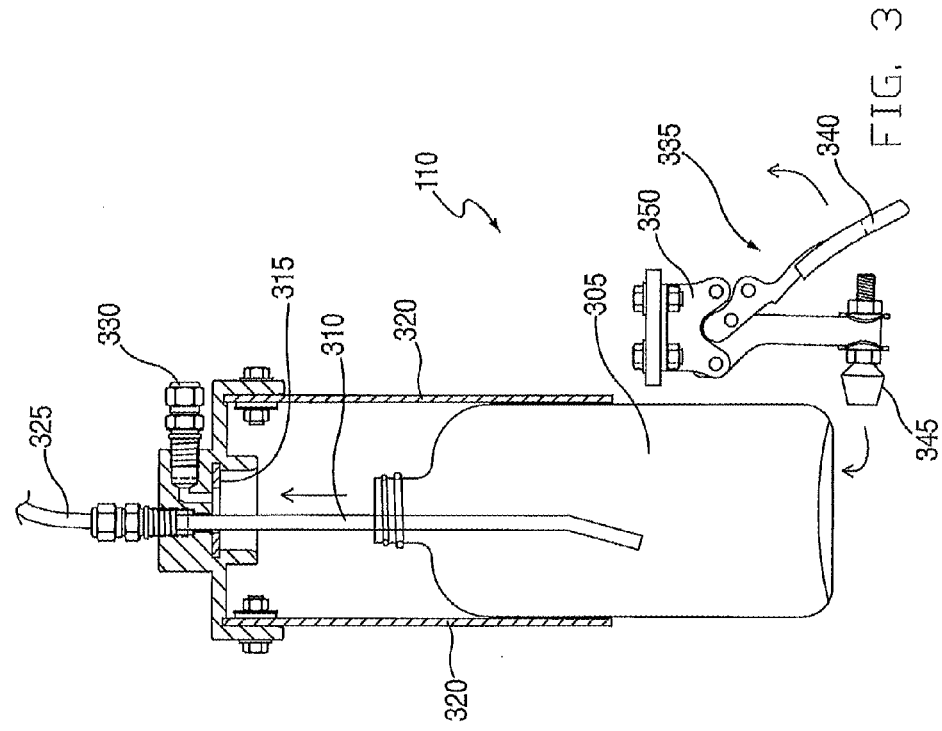

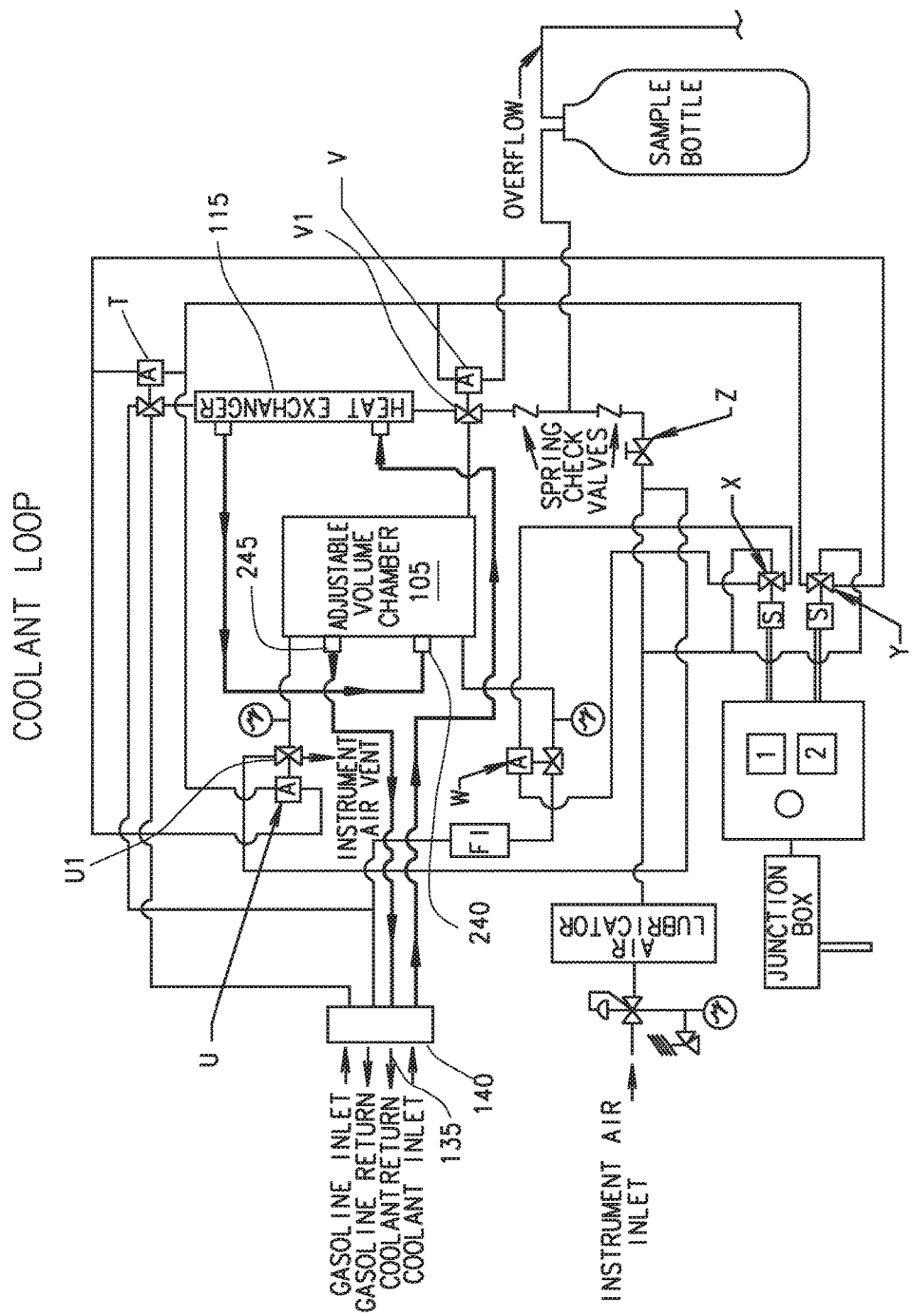
F I G . 7

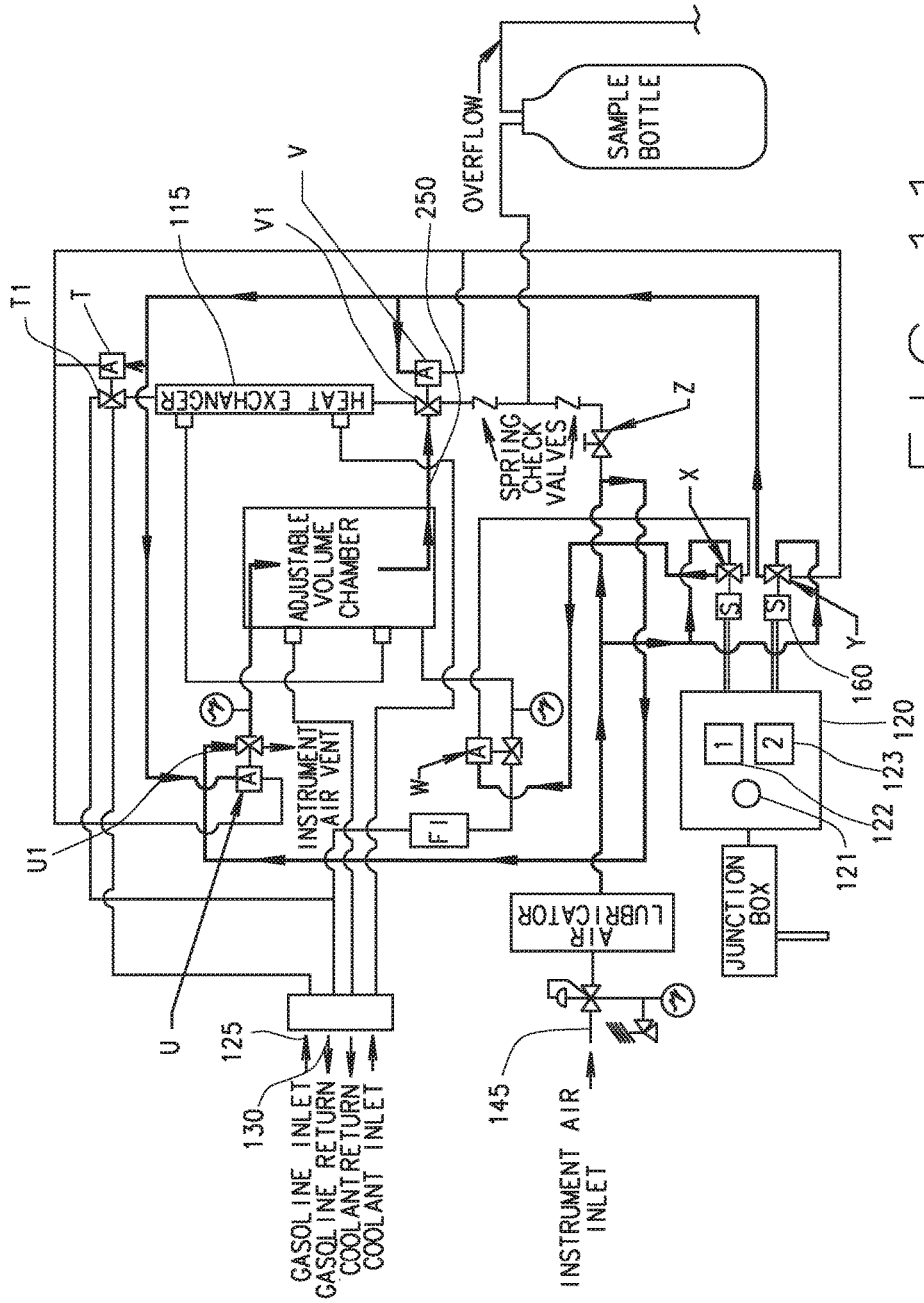
F I G. 11

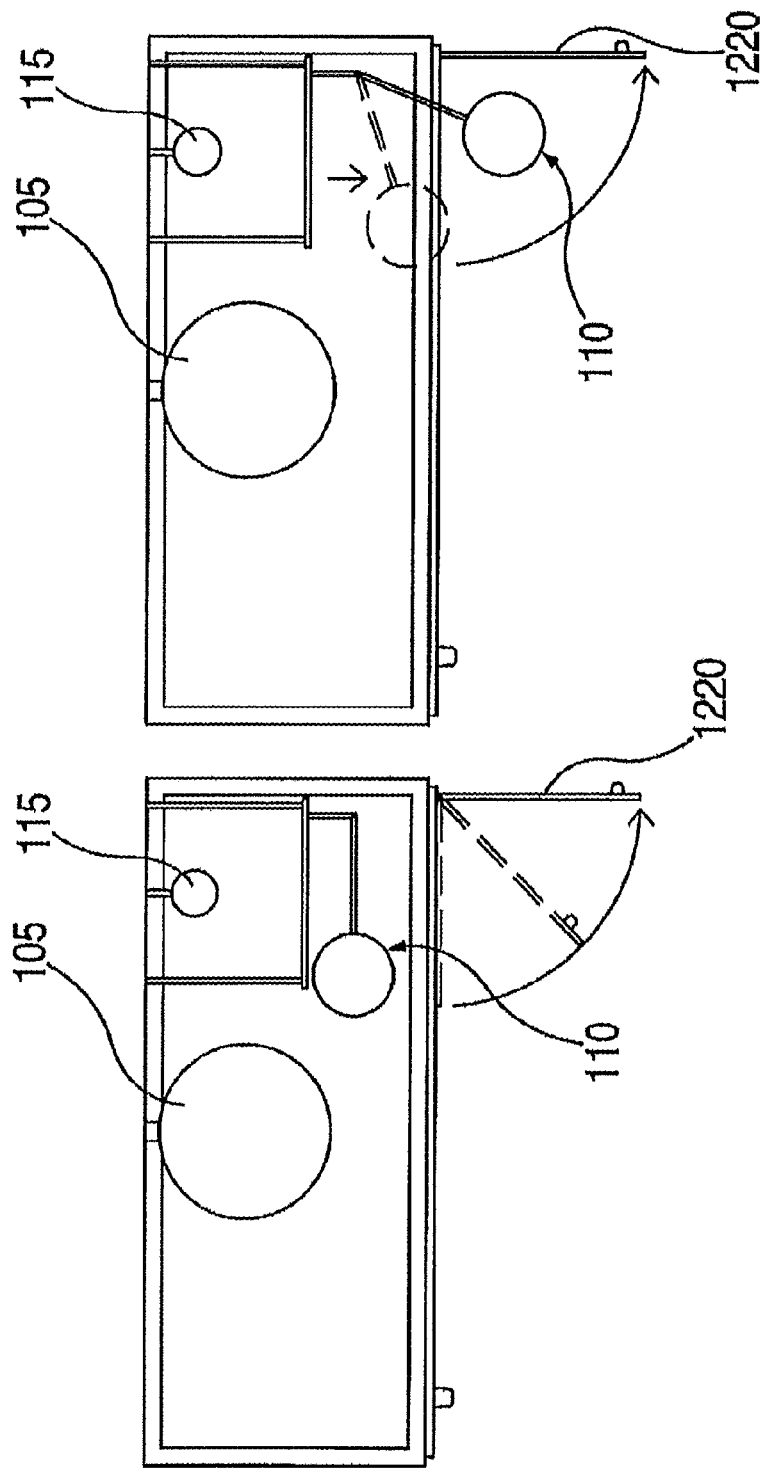

GASOLINE BLEND SPOT SAMPLING SYSTEM AND METHOD

CROSS REFERENCE TO RELATED APPLICATION

The present application is a divisional application of U.S. application Ser. No. 13/754,996, filed Jan. 31, 2013; now U.S. Pat. No. 9,255,862 entitled "GASOLINE BLEND SPOT SAMPLING SYSTEM AND METHOD" all of which is incorporated by reference herein in its entirety.

FIELD OF THE INVENTION

The present invention relates to gasoline blend spot sampling system and method and, more particularly, to a sampling system which includes an adjustable volume container to control the volume of a gasoline sample collected in an open-mouthed bottle.

BACKGROUND OF THE INVENTION

Refineries use crude oil as a feedstock and produce gasoline and other products. For quality control and other purposes, refineries take on-line samples of gasoline as it is blended. Refineries generally also take manual spot samples of gasoline for retention purposes using spot sampling systems. These manual spot samples are usually conducted in accordance with ASTM D 323-8 entitled "Standard Test Method for Vapor Pressure of Petroleum Products (Reid Method)".

Gasoline blend manual spot sampling systems are produced by Dopak located in Holland and Houston, Tex. The Dopak Process Sampler Type S23 is used for manual spot sampling of gasoline for retention purposes. Manual spot sampling systems are also produced by Texas Sampling Systems (TSS) of Victoria, Tex. TSS produces a manual Continuous Sample Apparatus, model number TSS MD-Flow Thru Sampler for taking manual spot samples of gasoline for retention purposes. TSS owns the following patents for a manual spot sampling system: U.S. Pat. Nos. 5,301,560; 5,431,067 and 5,433,120. These three patents use a four-way valve to control flow, and a closed container which uses a septum-like stopper to collect the sample via a needle pierced through the septum. Importantly, in these three patents, the volume of sample is fixed based on the piping design. To change the amount of sample, the piping must be changed. There is a need for a better manual spot sampling apparatus to take retention samples of gasoline which do not require bottles with septum-like stoppers to receive the sample, and which allow the volume of the sample to be changed as desired without modifying the structure of the system.

TSS also owns U.S. Pat. No. 5,361,643 entitled LPG Sampling System which is not relevant to the present inquiry. A search located the following additional references: U.S. Pat. Nos. 4,440,032; 5,945,611; 4,077,263; 4,101,282; 4,651,574; 4,355,539; 4,532,813; 5,665,314 and 6,682,939.

SUMMARY OF THE INVENTION

The present invention relates to a gasoline blend semi-automated spot sampling system, hereinafter referred to as a "gasoline sampler." In one embodiment, the gasoline sampler uses an adjustable volume mechanism to allow for an operator to adjust the volume of gasoline sampled, as needed. Thus, the sample amount that can be drawn may vary according to the volume of the adjustable volume mechanism, up to a selectable volumetric capacity of the adjustable volume mechanism. Such structure allows for relatively easy adjustment of sample volume within a range defined by the capacity of the adjustable volume mechanism. In order to vary the sample amount beyond the capacity of the adjustable volume mechanism, a different adjustable volume mechanism with a different volume need only be substituted into the system. Thus, adjustment of sample volume to a level beyond that of even a given adjustable volume mechanism requires only the replacement of a single component, and avoids the need to rework pipes. Additionally, an open mouthed sample bottle may be used to hold the retention sample of gasoline.

Preferably, when a sample is not being drawn and the system is on standby, the gasoline passes through a gasoline fast loop which preferably runs continuously to keep the gasoline in the lines fresh at all times. The gasoline flows in from the gasoline source through an inflow tube, and is directed immediately back out to the source via a first three-way valve connected to an outflow tube. However, when a sample is to be taken, the first three-way valve switches to direct the gasoline into a heat exchanger instead of directly back out to the gasoline source. The gasoline is cooled within the heat exchanger, at which point it leaves the heat exchanger and is directed by a second three-way valve into a gasoline chamber of the adjustable volume mechanism. For an initial period, the gasoline passes through the gasoline chamber and out of the adjustable volume mechanism to be routed out the outflow tube to the gasoline source. This initial period results in a temporary purge loop which flushes the pipes, heat exchanger, and adjustable volume mechanism of any old gasoline which may have remained therein. A timer may be used to determine the duration of the purge loop, as would be understood, although one to two minutes is generally sufficient.

After the initial period, the gasoline outflow from the adjustable volume mechanism is shut off by the timer, and a piston inside the gasoline chamber retracts to expand the fillable volume of the gasoline chamber. By controlling the piston's retraction distance, the fillable volume of the gasoline chamber is also controllable. This allows for easy manual adjustment of the specimen volume without substantial reworking of pipes. The gasoline thereby flows from the inflow tube through the heat exchanger, and then through the second three-way valve into the gasoline chamber, up to the desired volume. Once the desired gasoline volume within the gasoline chamber of the adjustable volume mechanism is reached, the three-way valves flip to prevent further gasoline traveling to the heat exchanger and from the heat exchanger to the adjustable volume mechanism. Instead, the second three-way valve allows for the gasoline in the gasoline chamber to be expelled from the adjustable volume mechanism by plunging the piston. The gasoline exits the gasoline chamber, travels through the flipped second three-way valve and enters the sample bottle. The first three-way valve may also flip back routing the inflow of gasoline through the outflow tube to the source when the second three-way valve redirects the gasoline into the sample bottle.

The system also preferably includes coolant lines which feed coolant to the heat exchanger to cool the gasoline therein. The coolant is preferably about a 50/50 mix of water and glycol and is preferably between about 25 degrees and 40 degrees Fahrenheit, but could be other coolants and other temperatures as are known in the art. Such coolant is also preferably used to cool the adjustable volume mechanism. In one embodiment, the adjustable volume mechanism includes one or more coolant cavities proximate to the gasoline chamber. By feeding coolant through the one or more coolant cavities, the gasoline chamber is also cooled. Alternatively, the coolant cavities may reside in a separate structure which is proximate to the adjustable volume mechanism. The coolant may run in series or in parallel to the heat exchanger and coolant cavities.

The system may be controlled by a control box which includes a button depressible by an operator to initiate the sampling sequence. The control box preferably includes two timers which control various valves within the system. The system preferably does not utilize four-way valves, as these are more expensive than three-way valves, although it is understood that the invention could be easily adapted to different types of valves as would be understood. However, the ability to use three-way valves instead of more expensive valves is a major advantage of the system.

DESCRIPTION OF THE DRAWINGS

FIGS. 3 and 4 are cross-sectional views of a sample collection assembly in its disengaged and engaged states, respectively, constructed according to the teachings of the present invention.

FIG. 7 is a schematic diagram showing one embodiment of a coolant loop, according to the teachings of the present invention.

FIG. 11 is a schematic diagram showing one embodiment of the discharge of a captured gasoline sample into a sample container, according to the teachings of the present invention.

FIGS. 14-16 are simplified top-plan views of the cabinet of FIG. 12 showing the spacing and position of several components therein, according to the teachings of the present invention.

It should be understood that the present drawings are not necessarily to scale and that the embodiments disclosed herein are sometimes illustrated by fragmentary views. In certain instances, details which are not necessary for an understanding of the present invention or which render other details difficult to perceive may have been omitted. It should also be understood that the invention is not necessarily limited to the particular embodiments illustrated herein. Like numbers utilized throughout the various figures designate like or similar parts or structure.

DETAILED DESCRIPTION

Figure 1:
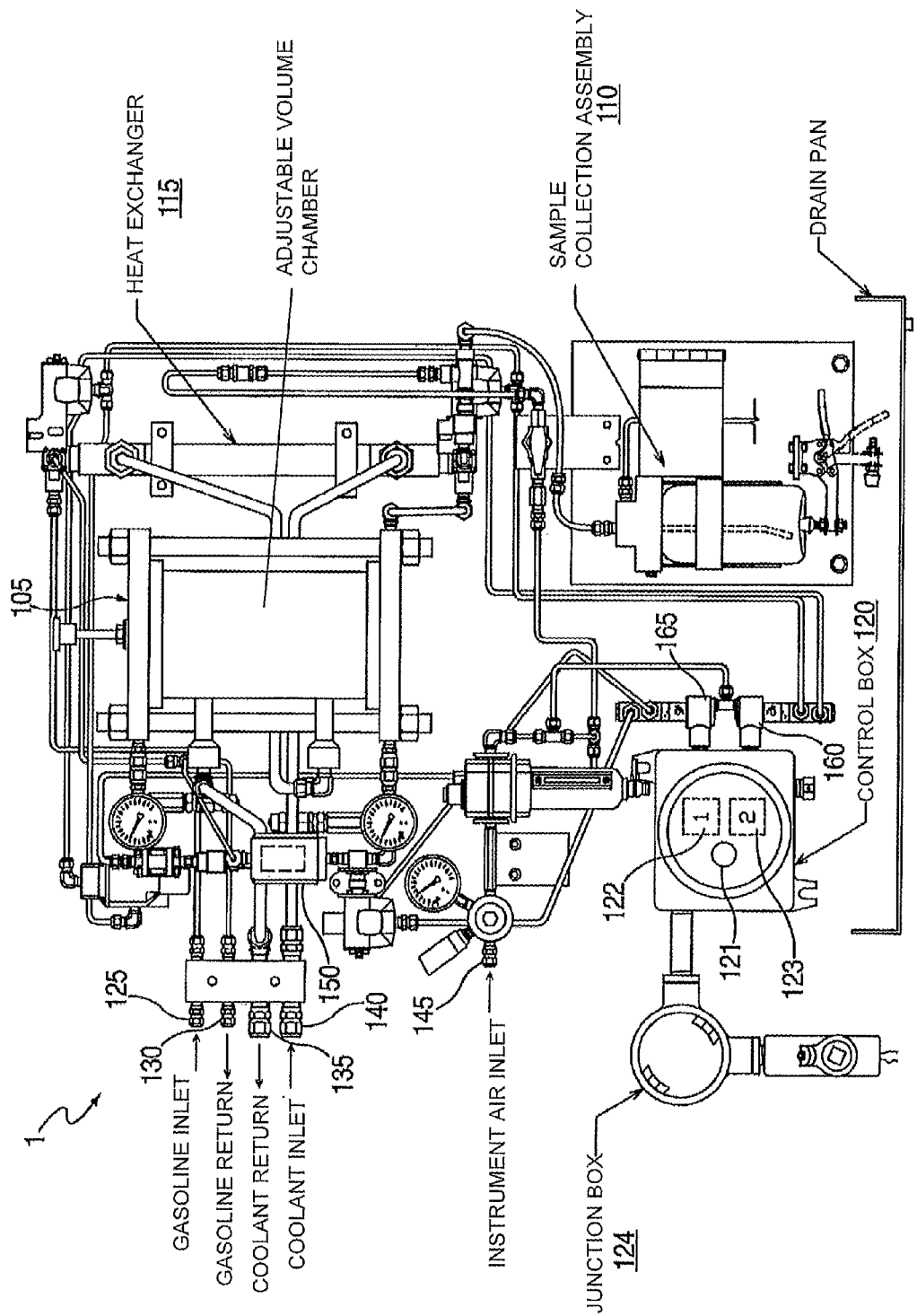
FIG. 1 is an overview diagram of one embodiment of the gasoline blend spot sampling system according to the teachings of the present invention.
Figure 5:
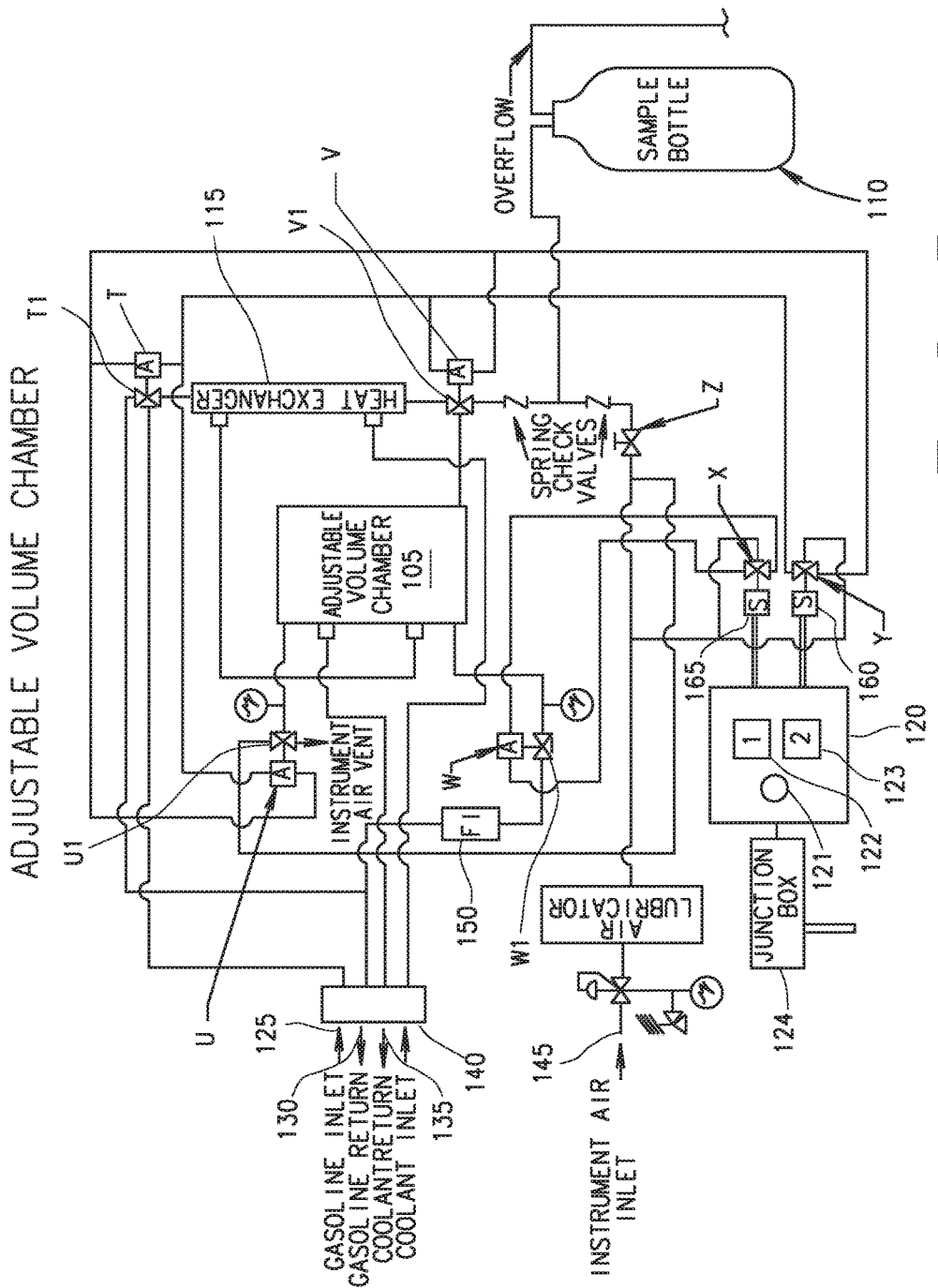
FIG. 5 is a schematic diagram of the system of FIG. 1

Referring now to the drawings and, more particularly, to FIGS. 1 and 5, an embodiment of a gasoline sampler system 1 is shown as constructed according to the teachings of the present invention. Gasoline sampler system 1 includes an adjustable volume mechanism 105 which is in fluid communication with a sample collection assembly 110. A heat exchanger 115 is also provided, as well as a control box 120. Control box 120 preferably includes a start button 121, and first and second timers 122, 123 as will be explained in further detail below. Timers 122 and 123 are connected to solenoids 165 and 160, respectively. The control box 120 receives power from junction box 124, and preferably communicates with external systems via junction box 124 as well. Various I/O ports are also provided, such as gasoline inlet 125, gasoline return 130, coolant inlet 140, coolant return 135 and instrument air inlet 145. A viewing window with internal flow indicator 150 is also provided which allows a user to determine if gasoline is purging out of the gasoline sampler system and/or view the gasoline which exits the adjustable volume mechanism 105.

Figure 2:
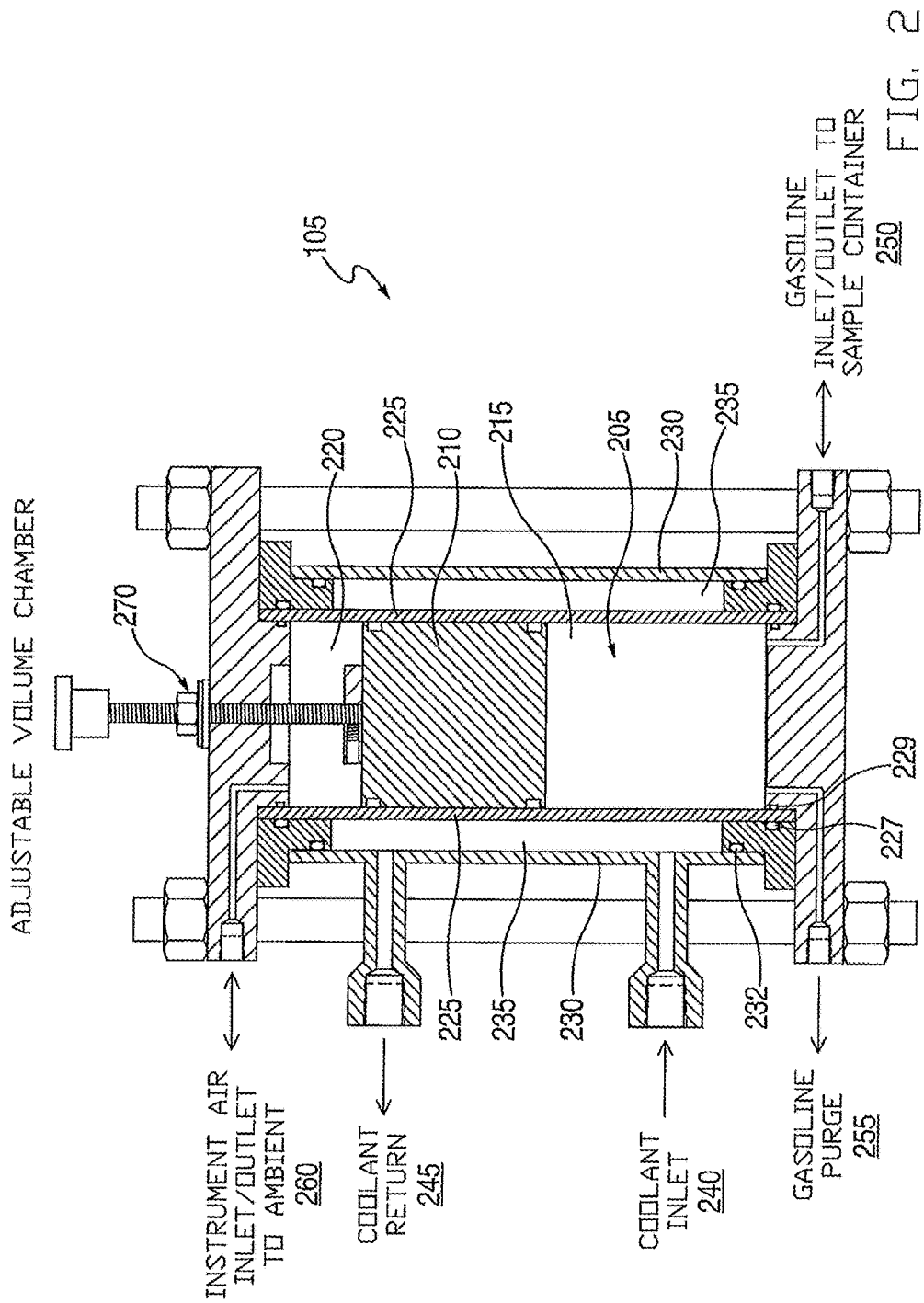
FIG. 2 is a cross-sectional view of one embodiment of an adjustable volume mechanism according to the teachings of the present invention.

As can be seen in FIG. 2, the adjustable volume mechanism 105 includes a gasoline chamber 205 which is divided by a piston 210 into a liquid section 215 below the piston, and a gas section 220 above the piston 210. The piston 210 preferably seals the liquid section 215 from the gas section 220 by sealing against the gasoline chamber wall 225. Surrounding the gasoline chamber wall 225 is a coolant cavity wall 230, defining a coolant cavity 235 between the coolant cavity wall 230 and the gasoline chamber wall 225. As coolant is circulated through the coolant cavity 235, the gasoline chamber 205 and its contents are cooled. As shown, the coolant cavity 235 is integral with the adjustable volume mechanism 105. However, this need not be the case, and the gasoline chamber 205 of the adjustable volume mechanism 105 may be separate from the coolant cavity 235 such that an adjustable volume mechanism merely resides in proximity to a coolant cavity 235. It is believed that better cooling performance results from an adjustable volume mechanism 105 with integral gasoline chamber 205 and coolant cavity 235 as shown in FIG. 2. In the construction as shown, the location of the seal 227 between the gasoline chamber wall 225 and the rest of the adjustable volume mechanism 105 is different than the location of the seal 232 between the coolant cavity wall 230 and the rest of the adjustable volume mechanism 105. Thus, there may be three different seals 227, 229, 232 in three different locations for the gasoline chamber wall 225 and the coolant cavity wall 230. If any of these three seals fail, there is no chance for cross-contamination because the other seal(s) would still be in place.

Coolant cavity 235 is fed by a coolant inlet port 240, and coolant exits the coolant cavity 235 via coolant return port 245. Similarly, gasoline enters the liquid section 215 of the gasoline chamber 205 via gasoline I/O port 250. During a gasoline purge discussed in detail below, gasoline exits the gasoline chamber 205 via gasoline purge outlet 255. An instrument air I/O port 260 is also provided for pressurizing and venting pressure from the gas section 220 of the gasoline chamber 205. The position of the piston 210 may thereby be controlled by competing pressures in the liquid section 215 as compared to the gas section 220. A higher air pressure in the gas section 220 than the liquid section 215 drives the piston 210 down, and vice versa. It is noted that the piston 210 may also or alternatively be hydraulically driven, or may be driven by an electrically powered motor. Additionally, the degree to which the piston 210 is able to move up or down within the gasoline chamber 205 may be adjusted via the piston adjustment assembly 270. The height to which the piston 210 can be pushed upward can be manually adjusted to modify the volume of gasoline which can be received by the liquid section 215 of the gasoline chamber 205, and/or the distance which the piston 210 may be plunged can be manually adjusted to modify the volume of gasoline which may be directed to the sample bottle by forcing it out of the liquid section 215 of the gasoline chamber 205. Either or both of these methods may be utilized to change the gasoline sample volume as desired.

FIGS. 3 and 4 illustrate a sample collection assembly 110. An open-mouthed bottle 305 may be used, as filled by a blunt-ended tube 310. In practice, the tube 310 is inserted into the mouth of the open-mouthed bottle 305, and the bottle 305 is fed up into a sleeve 320 where the mouth of bottle 305 seals against a seal 315. Thus, a septum is not necessary, and no needle is required. Sleeve 320 is designed both to prevent lateral movement of the bottle 305 to maintain a proper seal with seal 315, and to protect a user against a shattering bottle 305 as can sometimes happen due to thermal shock or defects in the bottle 305. Gasoline is fed to the tube 310 via a hose or tube 325. An overflow port 330 allows excess gasoline to exit the bottle 305 if too much gasoline is sent to the bottle 305.

The sample collection assembly 110 may also include a retention mechanism 335, which is designed to retain the bottle 305 in place as sealed with seal 315, and/or to push the bottle 305 up into place within sleeve 320. The retention mechanism 335 may include a lever section 340, a stopper section 345 and a base section 350. Preferably, the stopper section 345 includes a cushioned end which contacts the bottle 305 to hold it in place when the lever section 340 is actuated. In operation, moving the lever section 340 causes a rotation of the stopper section 345. The retention mechanism 335 may be structured other than as shown as would be understood by one of ordinary skill in the art.

Figure 6:
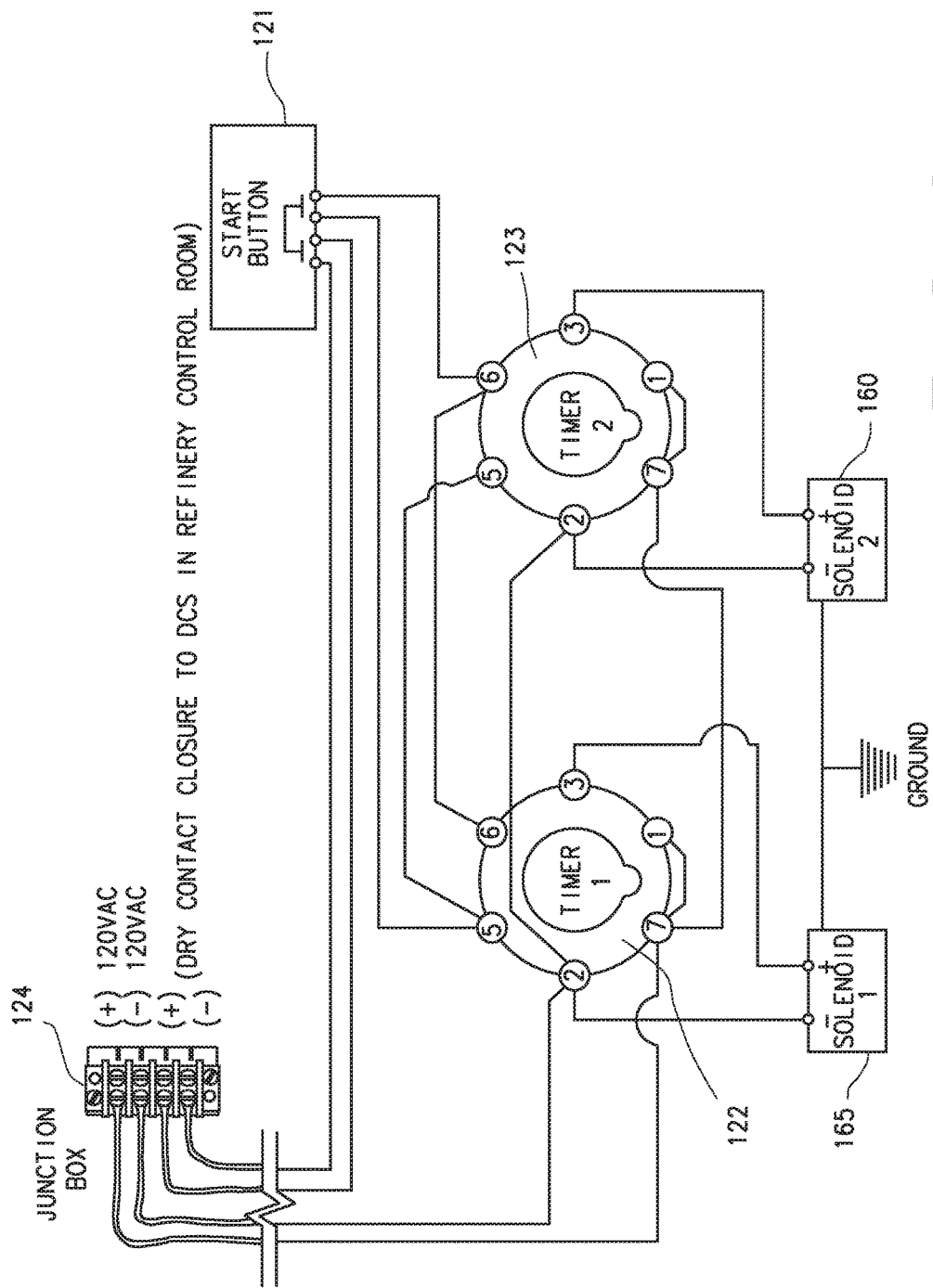
FIG. 6 is a schematic diagram of a timing mechanism.

FIG. 6 illustrates a schematic drawing of an example timer circuit, as would be understood. Start button 121 is connected to the first and second timers 122, 123 at pins 5 and 6 of the timers. The timers 122, 123 may be manually adjusted by an operator. When the start button is pressed, both timers draw current from the junction box 124 via pins 2 and 7, and solenoids 165 and 160 are actuated. The timers 122, 123 then begin counting down pre-set amounts of time (which may be different from one another), as is further discussed below. When the first timer reaches its pre-set time, it de-actuates the first solenoid 165. Similarly, when the second timer reaches its pre-set time, it de-actuates the second solenoid 160. In one embodiment, the timers 122, 123 are programmed mechanically, such that they require no electricity when not in operation. It is noted that solenoids 160, 165 may be actuated manually by a push-button located on each solenoid. Thus, in the absence of power or a malfunction in the timer, the solenoid may be actuated manually.

Alternatively, the timers 122, 123 may be any known timing mechanism as would be understood. Pressing the start button also preferably sends a signal to a control room or other central system indicating that the sample process has been initiated. This signal allows the central system to later match the sample with the time at which it was taken.

FIG. 7 illustrates an example coolant loop. Pneumatic instrument air is also shown although in FIG. 7, there is essentially no instrument air flowing. As can be seen, coolant flows from coolant inlet 140 to heat exchanger 115. From heat exchanger 115, the coolant flows to the coolant cavity 235 in the adjustable volume mechanism 105 via coolant inlet port 240, and later exits the coolant cavity 235 via coolant return port 245. From the coolant cavity 235, coolant returns to the coolant source via coolant return 135. In this way, coolant cools the contents of the heat exchanger 115 and the adjustable volume mechanism 105 before returning to the coolant source. This is preferably a continuous loop, and therefore there is no instrument air needed to actuate any valves or switches to reroute coolant, at least so far as is necessary to the understanding of this invention.

Figure 8:
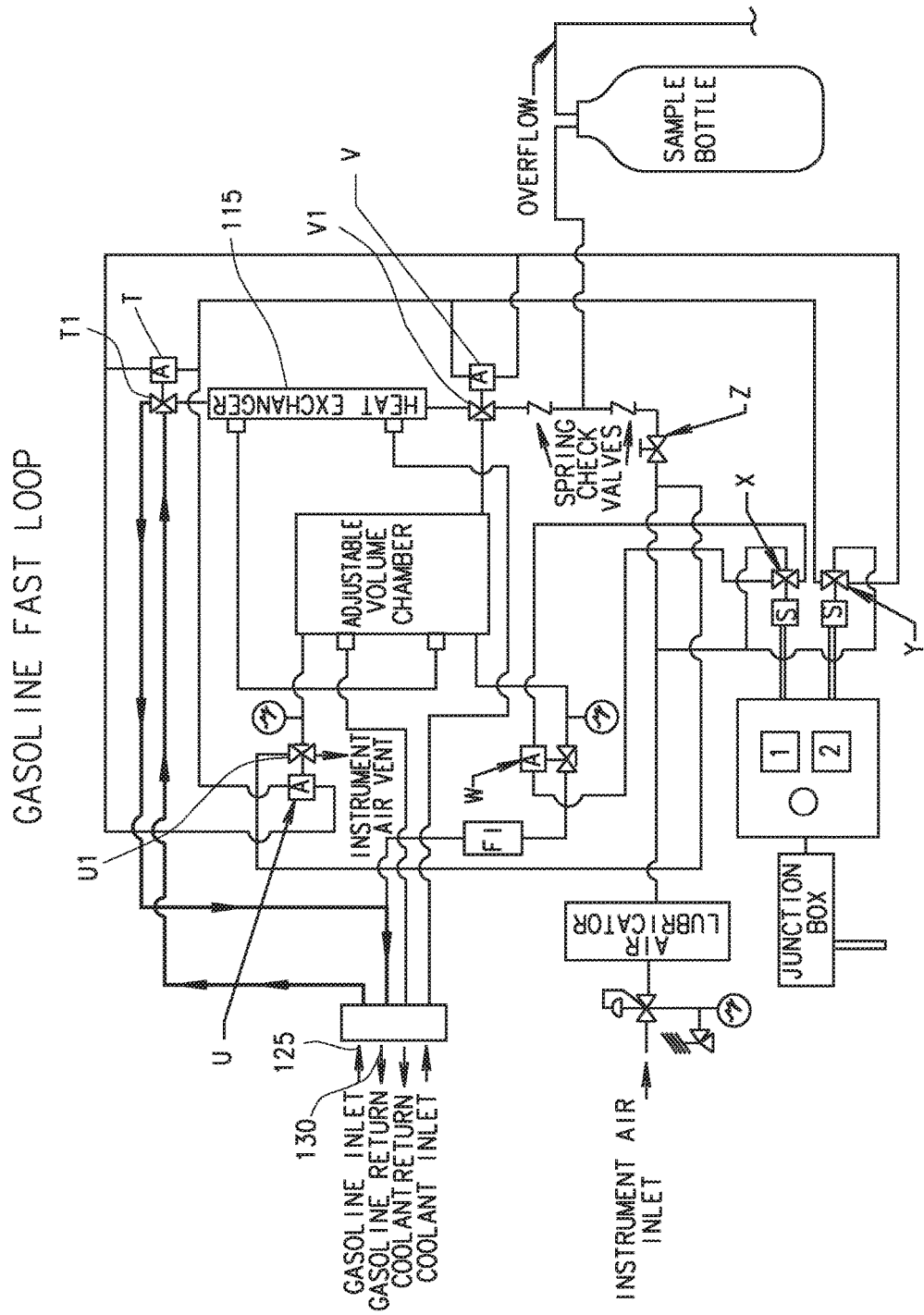
FIG. 8 is a schematic diagram showing one embodiment of a gasoline fast loop, according to the teachings of the present invention.

FIG. 8 illustrates an example gasoline fast loop. Again, there is no air flowing in this diagram. As can be seen, when no gasoline sample is being taken, gasoline travels in a fast loop from the gasoline source through gasoline inlet 125, through a first three-way valve T1, and back to the gasoline source via gasoline return 130. This maintains fresh gasoline in the pipes. First three-way valve T1 can be actuated by pneumatic actuator T, although once in position to route the gasoline back to the source, pneumatic actuator T is preferably not required to maintain the first three-way valve T1 in this position (hence the lack of instrument air flowing in FIG. 8).

Figure 9:
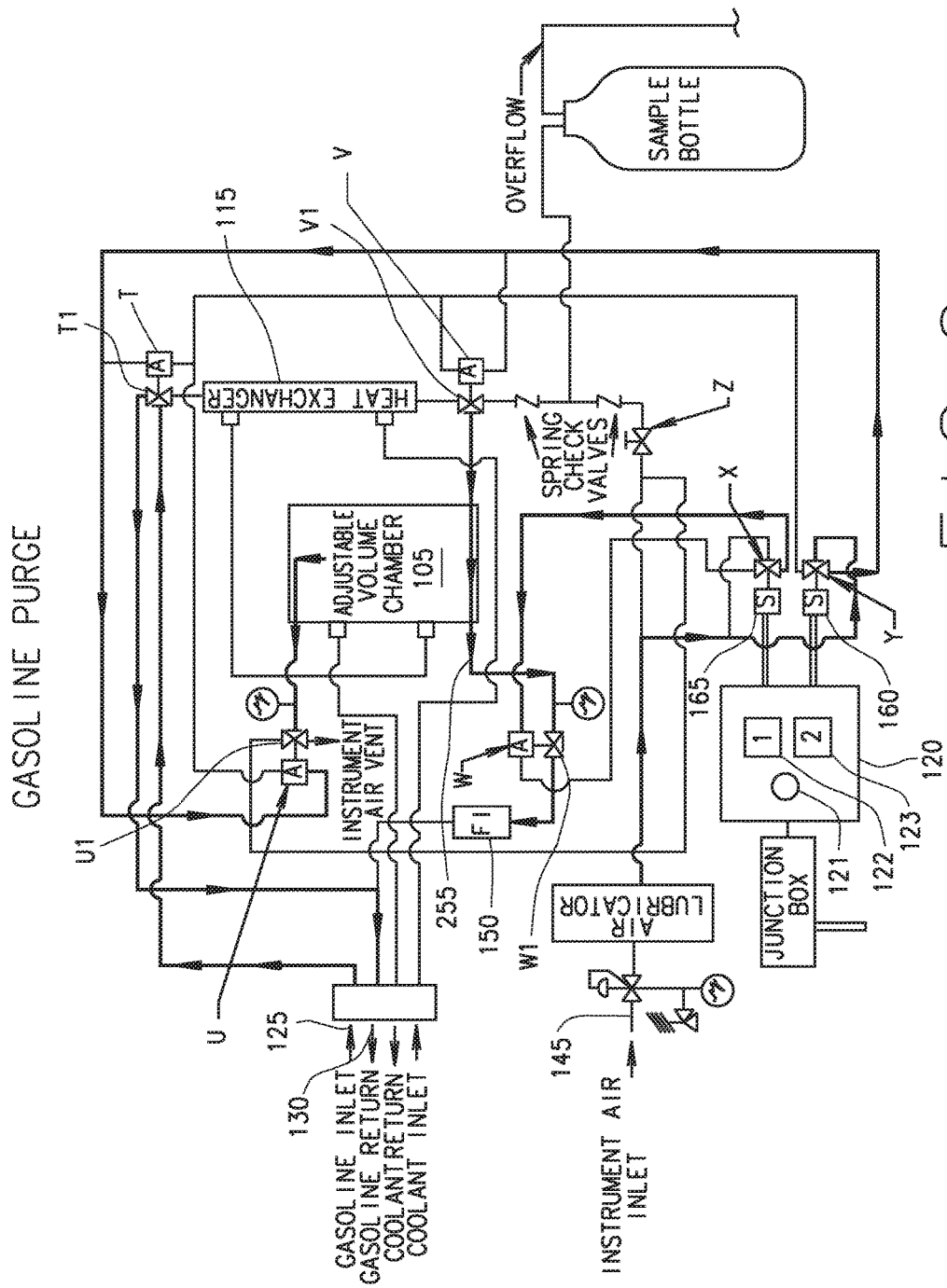
FIG. 9 is a schematic diagram showing one embodiment of a gasoline purge, according to the teachings of the present invention.

FIG. 9 illustrates an example gasoline purge loop. In FIG. 9, pneumatic instrument air is shown. In FIG. 9, the start button 121 has been pressed, which has caused timers 122, 123 to energize and begin counting. Upon energizing, timers 122, 123 cause solenoids 160, 165 to actuate the actuators on air valves Y and X, respectively. Air valve Y actuates to receive instrument air from the air source (preferably via air lubricator 905 to add an amount of lubricant to the air to help prolong the life of the valves), and direct such air to actuators T, U and V. Actuator T thus causes the first three-way valve T1 to switch, thereby directing gasoline from the gasoline inlet 125 to the heat exchanger 115, rather than back out via gasoline return 130. Gasoline therefore enters the heat exchanger 115 and is cooled by the circulating coolant therein. Gasoline then exits the heat exchanger 115, where it encounters the second three-way valve V1, which has been actuated by actuator V to route the gasoline into the I/O port 250 of the adjustable volume mechanism 105. Meanwhile, actuator U has caused the third three-way valve U1 to flip, allowing air pressure in the gas section 220 of gasoline chamber 205 to vent to atmosphere, thereby depressurizing the gas section 220.

Additionally, the first timer 122 has caused solenoid 165 to actuate air valve X to receive pneumatic instrument air from the air source 145 via air lubricator 905, which causes instrument air to be routed to actuator W, which opens valve W1. Thus, as gasoline flows into the gasoline chamber 205 of adjustable volume mechanism 105, it is able to flow out of outlet port 255, through valve W1, and back to gasoline return 130. This loop flushes any standing gasoline from the pipes, heat exchanger 115 and gasoline chamber 205 which may have remained from a previous sampling. Additionally, as the pressure in gas section 220 of gasoline chamber 205 has been vented to atmosphere, the pressure of gasoline traveling through the gasoline chamber 205 may be sufficient to force piston 210 slightly upward, again helping to clear any remaining gasoline from the system. Upon exiting the gasoline chamber 205, the gasoline may flow through a site glass or flow indicator 150 to allowing the gasoline flush to be viewed by an operator. In this way, an operator may be able to visually confirm that substantially all remaining gasoline has been flushed, such as based on the color of the gasoline exiting the gasoline chamber 205.

Figure 10:
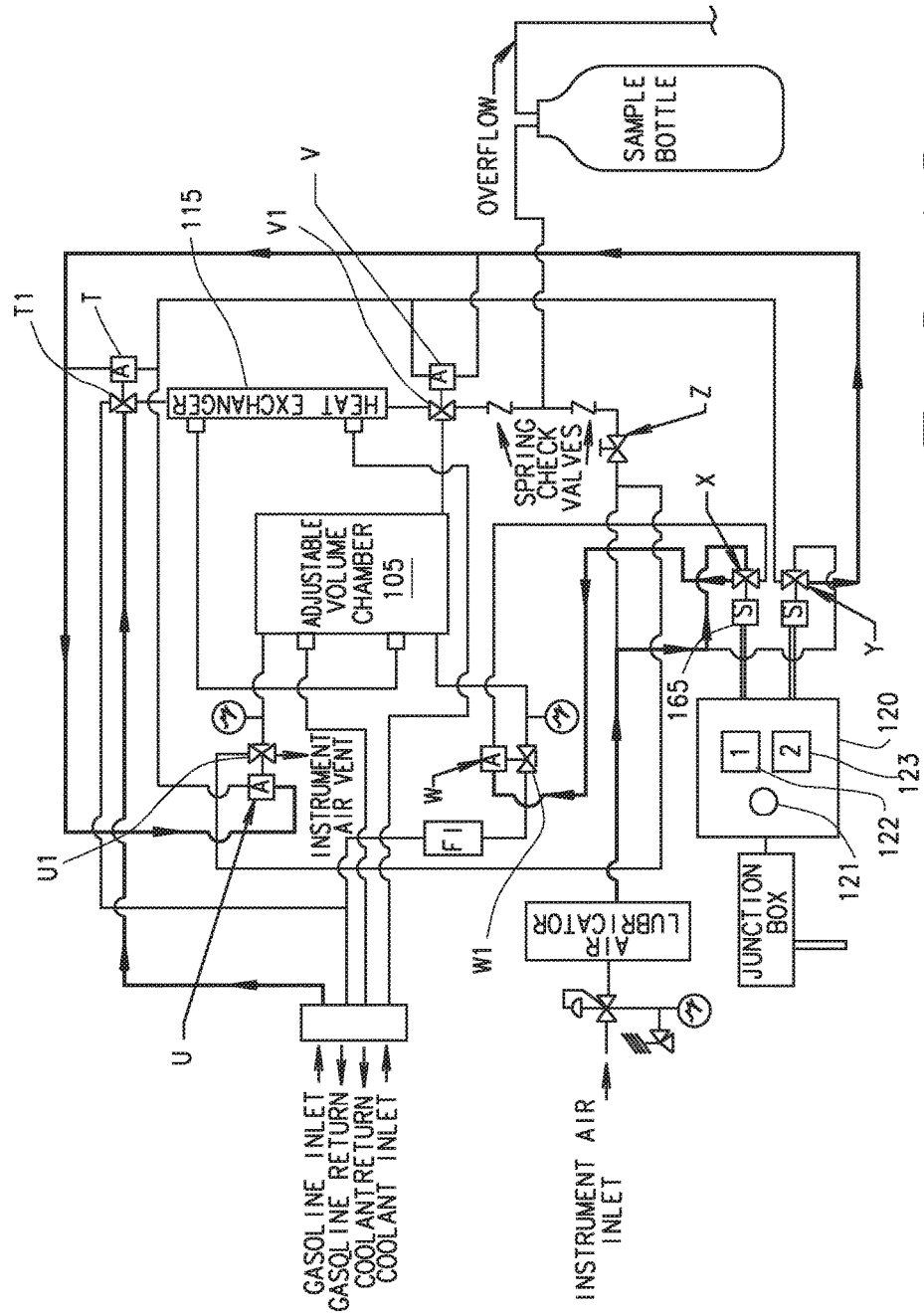
FIG. 10 is a schematic diagram showing one embodiment of a volumetric measurement and capture of a gasoline sample, according to the teachings of the present invention.

FIG. 10 illustrates an example volumetric gasoline capture schematic and the flow of instrument air associated with same. In FIG. 10, the first timer 122 has expired, ending the purge loop and causing solenoid 165 to flip air valve X. Valve X thereafter routes pneumatic instrument air to actuator W such that actuator W closes valve W1, which cuts off the outflow of gasoline from the gasoline chamber 205 of the adjustable volume chamber 105. As the second timer 123 has not yet expired, three-way valves T1, U1 and V1 all remain in the same position as in FIG. 9. As such, gasoline is still routed through the heat exchanger 115 and into the I/O port 250 of the adjustable volume mechanism 105. However, as gasoline cannot continuously exit the gasoline chamber 205 and return to the gasoline source due to closed valve W1, gasoline accumulates in the liquid section 215 of gasoline chamber 205. Also, as the third three-way valve U1 is in position to allow pressure in the gas section 220 to vent to atmosphere, the pressure of the volume of accumulating gasoline in the liquid section 215 is capable of forcing the piston 210 further upward, expanding the liquid section 215 and the fillable volume of the gasoline chamber 205. As noted above, the distance which the piston 210 can be forced up may be manually adjustable via the piston adjustment assembly 270, to adjust the fillable volume of the liquid section 215 of the gasoline chamber 205.

FIG. 11 illustrates a gasoline sample bottling schematic and the flow of instrument air associated with same. In FIG. 11, the second timer 123 has expired, causing solenoid 160 to actuate air valve Y. Valve Y thereafter routes pneumatic instrument air to actuators T, U and V to cause them to flip the first, second and third three-way valves T1, U1 and V1 back to their original states. Thus, three-way valve T1 begins routing gasoline from the gasoline inlet 125 directly back to gasoline return 130, reinitiating the gasoline fast loop discussed above. Three-way valve V1 flips to close off the path from heat exchanger 115 to the adjustable volume mechanism 105, and instead opens a path from the I/O port 250 of the adjustable volume mechanism 105 to the sample collection assembly 110. Simultaneously, three-way valve U1 flips to cut off the exhaust from the gas section 220 of the gasoline chamber 205, and instead opens a path from the instrument air inlet 145 through the instrument air I/O port 260 and into the gas section 220 of the gasoline chamber 205. By increasing the air pressure within gas section 220, the piston 210 is forced down, expelling the gasoline from the liquid section 215 of the gasoline chamber 205. As noted above, the downward distance which the piston 210 can be forced may be adjusted by the piston adjustment assembly 270 to control the volume of liquid expelled. As valve W1 remains closed, the only exit for the gasoline is the I/O port 250 of the adjustable volume mechanism, where the gasoline flows to the tube 325 of the sample collection assembly, and into bottle 305 via the blunt-end tube 310.

Figure 12:
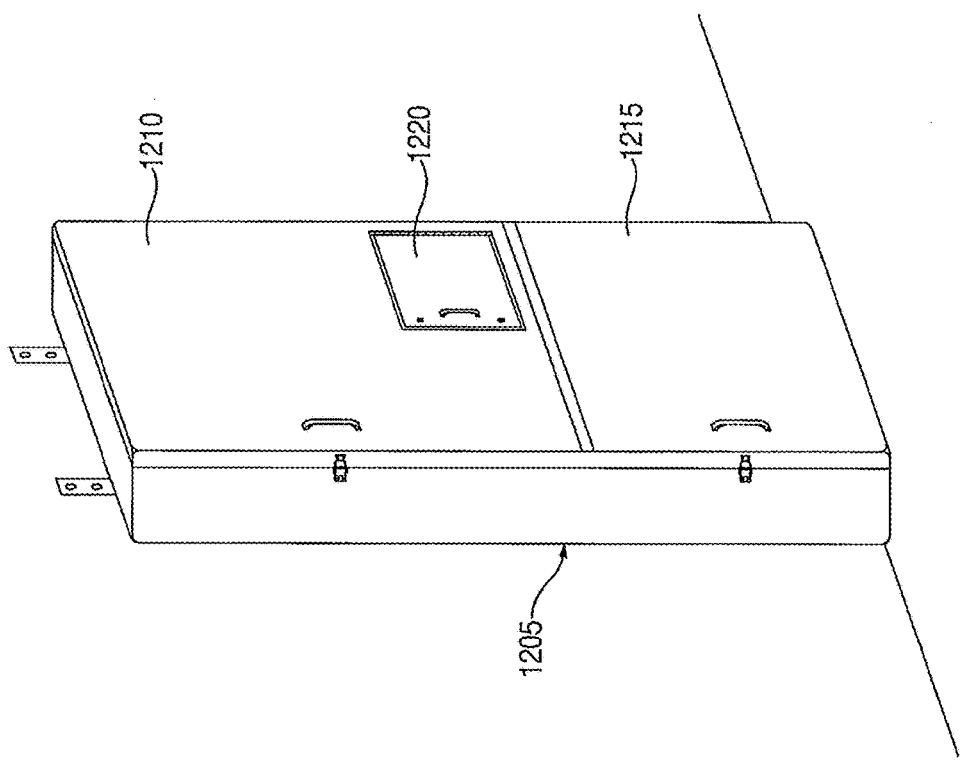
FIG. 12 is a perspective view of an example external insulated cabinet which may be used to house at least some of the components of the system, according to the teachings of the present invention.

FIG. 12 illustrates an embodiment of an external insulated cabinet 1205 which may be used to house at least some of the components of the above discussed system. As discussed above and as will be understood, keeping the gasoline in the system cool is an important issue. Exposing as little of the system as possible to external air can help keep cooling costs low while still maintaining a sufficiently low temperature throughout most of the system. Preferably, (at least a portion of) the gasoline pipes may be housed within a temperature controlled building, with cabinet 1205 residing on an outside wall. Only those pipes necessary would extend through the wall of the building and into cabinet 1205. Preferably, even cabinet 1205 is insulated to retain as much of the cooler temperature as possible. While the cabinet has upper and lower doors 1210, 1215 which can be opened as needed, in a preferred embodiment only smaller door 1220 would need to be opened to receive a sample. This lets out as little cool air as possible.

Figure 13:
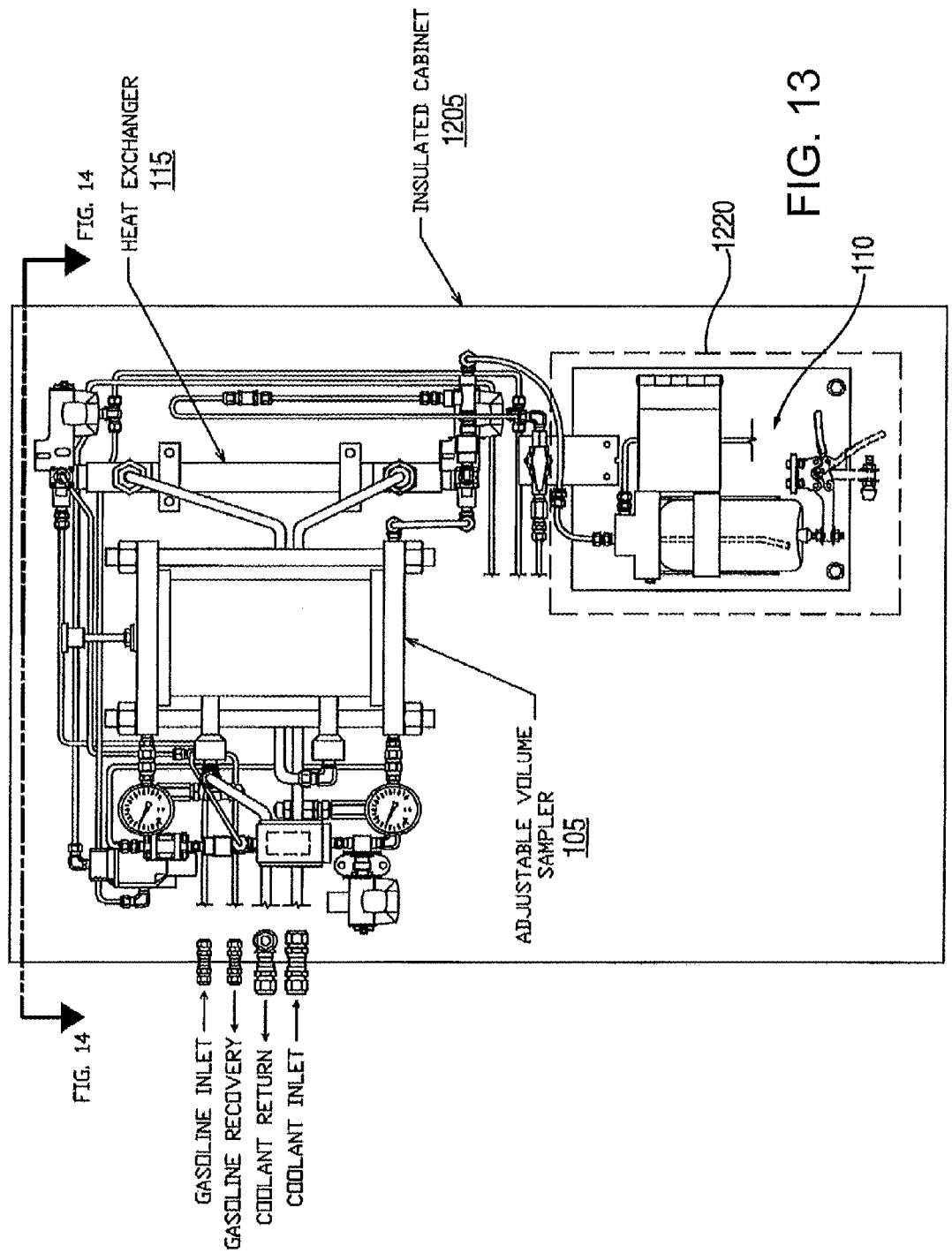
FIG. 13 is an overview diagram of example contents of the insulated cabinet of FIG. 12, according to the teachings of the present invention.

For example, FIG. 13 illustrates an example gasoline sample system as positioned within a cabinet 1205. As can be seen, many of the components discussed above may be positioned within the cabinet 1205, but the sample collection assembly 110 is specifically located proximate the smaller door 1220. A user may open the door 1220 to access the sample, and need not open the entire cabinet 1205. As such, preferably only a small amount of cool air is lost.

Figure 14:
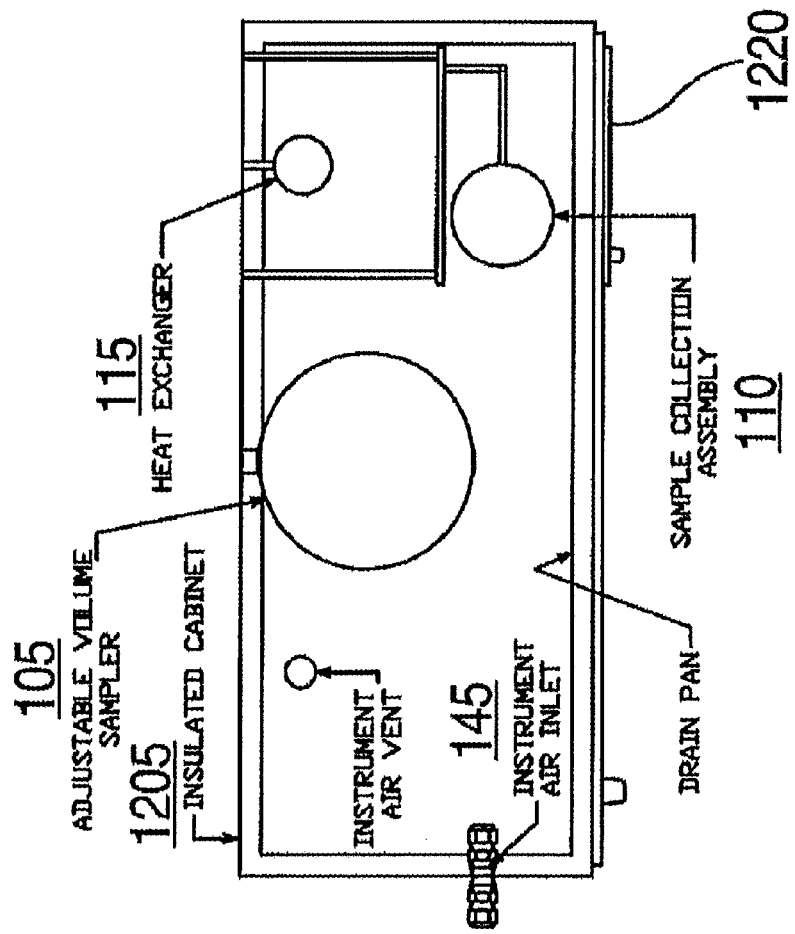

FIGS. 14-16 illustrate top plan views of cabinet 1205. FIG. 14 is taken across line 14-14 in FIG. 13, and shows the adjustable volume mechanism 105, heat exchanger 115, sample collection assembly 110, the instrument air inlet 145, cabinet 1205 and smaller door 1220. As can be seen in FIG. 15, door 1220 swings open, and in FIG. 16, the sample collection assembly 110 swings out to allow the user to remove the bottle 305. The user may then replace the sample bottle 305 with an empty bottle and/or close the door 1220.

Additionally, various gauges are illustrated in, for example, FIGS. 1, 5, etc. Such gauges would be known to one of ordinary skill in the art. However, their placement can allow for proper/better use of the disclosed sampling system. For example, rate gauges can confirm to a user that gasoline or coolant is flowing at a proper rate at a given location, thus telling the user that the valves are properly positioned. Additionally, a pressure gauge which measures the pressure within the gas section 220 of the gasoline chamber 205 may indicate to a user that the piston is likely retracted or plunged.

Thus, there has been shown and described several embodiments of a novel gasoline blend spot sampling system and method. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

The invention claimed is:

1. A method for sampling gasoline comprising the steps of:
   causing gasoline to switch from running through a fast-loop from a source back to the source, to running from the source through a heat exchanger;
   cooling said gasoline in the heat exchanger;
   passing said gasoline through the heat exchanger and a gasoline chamber in an adjustable volume mechanism for a period of time to flush any gasoline remaining from a previous sampling run from the heat exchanger and gasoline chamber;
   closing off an outflow from the gasoline chamber after the period of time, so as to cause gasoline to collect in the gasoline chamber and force a piston in the gasoline chamber toward a retracted position;
determining when the volume of gasoline in the gasoline chamber has reached a predetermined volume; and
forcing the piston toward an extended position to force gasoline out of the gasoline chamber into a sample bottle for collection.

* * * * *

UNITED STATES PATENT AND TRADEMARK OFFICE
CERTIFICATE OF CORRECTION

| | |
|---|---|
| PATENT NO. | : 9,651,459 B2 |
| APPLICATION NO. | : 14/995315 |
| DATED | : May 16, 2017 |
| INVENTOR(S) | : James T. Klentzman |

It is certified that error appears in the above-identified patent and that said Letters Patent is hereby corrected as shown below:

In the Specification

In Column 2, Line 41 replace the term "Tillable" with -- fillable --

Signed and Sealed this
Third Day of October, 2017

Joseph Matal
*Performing the Functions and Duties of the*
*Under Secretary of Commerce for Intellectual Property and*
*Director of the United States Patent and Trademark Office*